(12) United States Patent
Burg

(10) Patent No.: US 6,991,652 B2
(45) Date of Patent: Jan. 31, 2006

(54) TISSUE ENGINEERING COMPOSITE

(76) Inventor: Karen J. L. Burg, 125 Knollwood Dr., Clemson, SC (US) 29631

( * ) Notice: Subject to any disclaimer, the term of this patent is extended or adjusted under 35 U.S.C. 154(b) by 105 days.

(21) Appl. No.: 09/879,360

(22) Filed: Jun. 12, 2001

(65) Prior Publication Data

US 2002/0022883 A1 Feb. 21, 2002

Related U.S. Application Data

(60) Provisional application No. 60/211,147, filed on Jun. 13, 2000.

(51) Int. Cl.
*A61F 2/12* (2006.01)

(52) U.S. Cl. ............... 623/8; 623/11.11; 623/23.72; 623/23.76; 424/722; 424/424

(58) Field of Classification Search ............ 623/8, 623/11.11, 23.72, 23.75, 23.76; 604/93; 424/400, 422, 423, 426, 428, 444
See application file for complete search history.

(56) References Cited

U.S. PATENT DOCUMENTS

| | | | |
|---|---|---|---|
| 4,352,883 A | * | 10/1982 | Lim |
| 5,290,827 A | * | 3/1994 | Shine |
| 5,658,329 A | * | 8/1997 | Purkait |
| 5,716,404 A | | 2/1998 | Vacanti et al. |
| 5,728,762 A | * | 3/1998 | Reich et al. |
| 5,858,746 A | * | 1/1999 | Hubbell et al. |

FOREIGN PATENT DOCUMENTS

WO  WO 98/12228  3/1998

OTHER PUBLICATIONS

Eppley et al., *Annals of Plastic Surgery*, 32:463-468 (1994).
Eppley et al., *Aesth. Plast. Surg.*, 18:413-416 (1994).

\* cited by examiner

*Primary Examiner*—Vincent Millin
*Assistant Examiner*—Lalita M. Hamilton
(74) *Attorney, Agent, or Firm*—Leigh P Gregory

(57) ABSTRACT

The invention provides a biocompatible composite for use in a living subject for purposes of repairing damaged tissues and reconstructing a new tissue. The composite includes a biodegradable or absorbable three-dimensional support construct, a liquid or viscous fluid forming a gel matrix or viscous fluid when delivered to an area of interest in a living subject. The biodegradable construct provides an ideal surface for cell or cell extract attachment, while the gel matrix or viscous fluid acts as both a carrier material and a separator for maintaining the space between the constructs as well as the structural integrity of the developing issue.

49 Claims, No Drawings

TISSUE ENGINEERING COMPOSITE

CROSS-REFERENCE TO RELATED APPLICATION

This application claims the priority under 35 U.S.C. § 119(e) to U.S. Provisional Application No. 60/211,147, filed Jun. 13, 2000, the entirety of which is incorporated herein by reference.

FIELD OF THE INVENTION

This invention generally relates to tissue engineering, and in particular to tissue engineering composites and methods of using the composites.

BACKGROUND OF THE INVENTION

Tissue engineering often involves delivering a gel material such as hydrogel into a defective area of the body or to a body area where repair or reconstruction is desired. The gel material can be used as a support matrix for the ingrowth of surrounding tissue cells. Often cells or tissues are also dispersed in the gel material and injected into the body along with the gel material.

Conventional materials such as hydrogels typically have a smooth surface with a low modulus and can readily flow to fill an irregular cavity. However, the smooth and low modulus surface of such hydrogels makes it difficult for cells to attach thereto. In addition, because of the low porosity of the hydrogel, diffusion of nutrients to incorporated cells and removal of wastes from incorporated cells is inhibited. As a result, the hydrogel can not effectively facilitate tissue growth and repair.

SUMMARY OF THE INVENTION

The present invention provides a composite for providing cells to a living subject. The composite includes a biocompatible three-dimensional porous constructs and a carrier. The construct may be acellular or, in preferred embodiments, the composite includes cells or tissue extracts. After delivery, cells in the living subject surrounding the composite grow into the carrier and attach to the surface and within the three-dimensional porous constructs, thereby forming new three-dimensional tissue.

The three-dimensional porous constructs are made from a biodegradable or absorbable, biocompatible materials including, both naturally derived materials as well as non-naturally derived materials. The constructs preferably are macroporous and support the adhesion, growth and migration of the transplanted cells as well as the ingrowth of the tissue cells surrounding the constructs. The constructs may take several forms, including but not limited to meshes, beads, or rods. An especially preferred porous support construct material is a collagen. Normally, the three-dimensional constructs are prepared such that they have dimensions small enough to pass through a conventional needle and thus can be injected in the area of interest in the living subject along with the carrier.

The carrier is a liquid or viscous fluid forming a gel matrix or viscous fluid when in the body of a living subject. Like the construct, the carrier may be made from both naturally derived materials as well as non-naturally derived materials. The viscosity of the liquid or viscous fluid is low enough such that the liquid or viscous fluid can be readily injected through a conventional needle. However, the viscosity of the liquid or viscous fluid should not be too low, lest the three-dimensional cell support structures can move freely within the gel matrix. Preferably, the liquid or viscous fluid has a viscosity of from about 10 to about 1000 cps.

In accordance with one embodiment of the invention, the three-dimensional constructs are seeded with cells and/or small tissue explants and/or cellular extracts, which can grow in or on the constructs while the constructs are gradually degraded and absorbed by the tissue or excreted by the body. As a result of the growth of the transplanted cells or tissues and the ingrowth of the cells from the surrounding tissue, a three-dimensional tissue can be formed. In another embodiment of the invention, the cells or small tissue explants are seeded in the carrier. In yet another embodiment of the invention, both the construct and the carrier are seeded with cells. In yet another embodiment of the invention both the construct and the carrier are acellular.

In the composites of the present invention, the constructs provide an ideal surface for cell attachment, while the carrier acts as both a delivery material and a separator for maintaining the space between the constructs. The carrier embeds the constructs dispersed therein and prevents undue compression of the constructs. As a result, the constructs are distributed three-dimensionally in the carrier, thus facilitating the formation of a three-dimensional tissue.

The composites allow both the growth of the transplanted cells or tissue explants and the ingrowth of the surrounding tissue cells. The composites gradually degrade or absorb within the body, yielding space for further tissue and cell growth. In addition, the composites are small enough such that the composite of this invention is readily injectable into a desired area in the body. Accordingly, the present invention provides a simple, non-invasive, and effective method for tissue repair and reconstruction. In another embodiment of this invention methods are provided for delivery of the composites to the area of interest in a living subject. A preferred method of delivery is by injection. The composition can be readily injected into a target area of the body of a subject to fill a void or cavity.

The composites of the present invention are suitable for various tissue engineering applications including tissue augmentation, tissue reconstruction, and tissue repair in, e.g., breast tissue, dental tissue, skin tissue, spinal disc tissue, soft tissue, cartilage, and bone tissue. It is also suitable as a bulking agent for incontinence.

It is an object of the present invention to provide a composite for delivery into a living subject.

Another object of the present invention is to provide a method of delivering cells or tissue to into a living subject.

The foregoing and other advantages and features of the invention, and the manner in which the same are accomplished, will become more readily apparent upon consideration of the following detailed description of the invention taken in conjunction with the accompanying examples, which illustrate preferred and exemplary embodiments.

DETAILED DESCRIPTION OF THE INVENTION

In accordance with the present invention, a composite is provided to a living subject comprising a three-dimensional support construct and a carrier.

The Support Construct

The constructs of the present invention are biocompatible three-dimensional porous materials. "Biocompatible" means that the material used for the components of the present invention does not substantially adversely affect any desired characteristics of the cells or tissues to be seeded within the construct, or the cells or tissues in the area of a living subject where the composition containing the constructs and gel matrix is to be delivered. It is also intended that the material used does not cause any substantially medically undesirable effect in any other areas of the living subject. The biocompatible materials may be synthetic or natural. The materials are chosen such that three-dimensional construct supports cell adhesion, growth, and migration. Preferably, the biocompatible materials used for the constructs should also be mechanically strong enough to support cells and to substantially maintain a predetermined desirable dimension. Generally, the methods for testing a material's biocompatibility and mechanical strength is well known in the art.

A biocompatible material used in the present invention may be nonabsorbable, i.e., its chemical structure remains substantially unchanged, and the physical structure of the construct made thereof remains substantially intact for at least about one year after the composition of this invention is injected into body of the living subject.

Preferably the biocompatible materials used in this invention are biodegradable or absorbable, and will be gradually degraded or absorbed after the carrier or constructs made thereof are delivered to an area of interest inside the body of a living subject. Such degradation should be in a controlled fashion. Preferably substantial degradation takes place only after sufficient cells have grown within the construct to form an organized three-dimensional tissue. In this manner, the degradation of the bioabsorbable material does not substantially interfere with the cell growth and movement within the constructs or carrier. Typically, the bioabsorbable material is substantially degraded (i.e., at least 50% of the biocompatible material is degraded into smaller molecules, or absorbed or excreted from the body) within one year after the injection of the composition into the desired area of the body of a living subject. Preferably, the absorbable material is substantially degraded or absorbed within 6 months after the injection, more preferably within about 3 months of the injection. Advantageously, the constructs and carrier are completely degraded or absorbed within one year after the injection.

Examples of suitable biodegradable or absorbable biocompatible materials for the constructs include, but are not limited to polylactide, chondroitin sulfate (a proteoglycan component), polyesters, polyethylene glycols, polycarbonates, polyvinyl alcohols, polyacrylamides, polyamides, polyacrylates, polyesters, polyetheresters, polymethacrylates, polyurethanes, polycaprolactone, polyphophazenes, polyorthoesters, polyglycolide, copolymers of lysine and lactic acid, copolymers of lysine-RGD and lactic acid, and the like, and copolymers of the same. Examples of suitable biodegradable or absorbable naturally derived biocompatible materials for the constructs include, but are not limited to chitosan, agarose, alginate, collagen, hyaluronic acid, and carrageenan (a carboxylated seaweed polysaccharide), demineralized bone matrix, and the like, and copolymers of the same.

Although non-biodegradable materials can be used in forming the support constructs, preferably biodegradable or bioabsorbable biocompatible materials are used such that the constructs are substantially biodegradable or bioabsorbable. Among the biodegradable, biocompatible materials enumerated above, collagen is especially desirable. Various types of collagens are known and commercially available. Collagens can also be prepared by conventional methods such as those disclosed in U.S. Pat. Nos. 3,934,852; 3,121,049; 3,131,130; 3,314,861; 3,530,037; 3,949,073; 4,233,360 and 4,488,911.

The three-dimensional support constructs allow both the growth of cells or tissue seeded therein and the ingrowth and attachment of the surrounding tissue cells. The support constructs of this invention can be in any three-dimensional shape so long as the construct has a size small enough to pass through a conventional needle. Preferably, the constructs have a size of no greater than about 1.5 mm in diameter, more preferably about 1.0 mm or less in diameter. Advantageously, the size of the construct is from about 50 μm to about 800 μm in diameter. For example, the construct can be spheres, particle beads, mesh, rods, triangles, threads, and cubes. Also, a combination of construct sizes and types may be employed.

Generally speaking, the material forming the construct should not react with materials in the carrier in a manner so as to adversely affect the structure and properties of the construct or the delivery of the carrier, or adversely affect the biocompatibility of the materials in the construct or carrier.

Preferably, the three-dimensional support constructs are porous having an interconnected macroporous structure formed by one or more biocompatible materials which constitutes the skeleton of the structure. There can be a plurality of macropores on the surfaces of the construct connecting the macropores within the construct so that exchange of molecules and cell migration can occur between inside of the construct and the surrounding environment. The diameter of the pores can range from about 10 μm to about 300 μm, preferably from about 25 μm to about 200 μm, more preferably from about 50 μm to about 100 μm.

The three-dimensional porous constructs can be made by any known techniques for producing small beads or other discrete structures. Suitable techniques include, but are not limited to, weaving, knitting, pressure or air shear spraying, extrusion, emulsification, and droplet formation techniques such as electrostatic droplet formation, droplet formation by gravity, droplet formation by centrifugal forces, droplet formation using Raleigh liquid jet instability techniques, and droplet formation using inertial forces. For example, suitable porous constructs are prepared from collagen materials by solidifying a collagen solution or dispersion into dry beads using any known drying techniques including but not limited to spray drying and freeze-drying. Collagen beads can also be formed by dropping collagen solution into a cross linking solution, e.g., $CaCl_2$, as is known in the art. Also, beads having larger sizes can be reduced to small sizes by, for example, grinding.

If porous constructs are desired, any techniques known for making a porous scaffold supporting cell growth can be used, with certain modifications of these methods to obtain the distinct features of the constructs of the present invention as specified above. Such modifications will be apparent to an ordinarily skilled person in the art apprised of the present disclosure.

Pores in the constructs can be formed during formation of the constructs, e.g., during the process of polymerization of one or more polymers using conventional methods for making macroporous structures. Alternatively, the macropores in the construct can be formed by dissolution of a polymer or removal of one material after polymerization. For example, two polymerization precursors (a matrix polymer precursor such as collagen, fibrin, etc., and a reversible gel polymer precursor such as alginate, gums, agarose, etc.) are polymerized together in an aqueous solution to form a three-dimensional structure. The reversible gel polymer is then dissolved and removed to form an insoluble, porous three-dimensional construct. Pores can also be generated by post polymerization techniques known to those skilled in the art.

The Carrier

The carrier is a liquid or viscous fluid that forms a gel or viscous fluid matrix. "Gel matrix" refers to a gel material, i.e., a colloid in which the disperse phase has combined with the continuous phase to produce a viscous semisolid jelly-like product. The gelling may partially occur prior to delivery to the living subject, then completely gel after delivery or the gelling may occur entirely after delivery. There are different methods of gelling the materials for use in this invention. For example, a chemical gelling agent may be used or other gelling may be caused to occur because of shifts in pH or temperature (so something may be ungelled at body temperature then injected, and then due to the higher temperature may gel). Combinations of gels or gels and fluids are possible. For example, using a combination of alginate and gelatin as the delivery vehicle—the gelatin is a thermo-reversible gel that will return to the liquid state at a higher temperature. This characteristic is useful in creating porous structure within the gel once delivered is advantageous for creating porosity within the carrier.

The carrier should have a viscosity of from about 10 to about 1000 cps, preferably from about 20 to about 750, more preferably from about 50 to about 500 cps at a temperature of about 37° C. As is known in the art, viscosity can be readily determined by conventional methods and viscometers such as Brookfield viscometer, Krebs-Stormer viscometer, and the like. Typically, the carrier has a density of from about 0.5 g/100 ml to about 9 g/100 ml preferably from about 1.0 g/100 ml to about 5 g/100 ml, and more preferably from about 1.5 g/100 ml to about 3 g/100 ml.

As will be apparent from the present disclosure, the viscosity and density of the carrier used in the present invention should be selected such that the carrier is easily delivered to the subject. Once delivered, the three-dimensional porous support constructs cannot move freely within the carrier. If the viscosity or density of the gel matrix is too high, it will make it difficult to deliver the gel matrix into the desired area of the living subject, and will prevent cell movement and ingrowth within the carrier. It may also unduly reduce the diffusion rate of cell nutrients or waste materials within the carrier. On the other hand, if the viscosity or density is too low, e.g., approaching those of Newtonian liquids, the carrier would not be effective in maintaining the spacing between the three-dimensional porous support constructs, or retaining the integrity of the developing tissue.

The carrier may be made from one or more biocompatible materials which can be biodegradable or absorbable, or non-biodegradable or non-absorbable. In addition, the biocompatible materials used for the carrier should be chosen such that the carrier formed thereof has the desirable viscosity and density described above.

Examples of suitable biodegradable, or absorbable, or non-degradable naturally derived biocompatible materials for the gel/fluid carrier include, but are not limited to agarose, alginate, collagen, carrageenan (a carboxylated seaweed polysaccharide), chitosan and derivatives thereof. Examples of suitable biodegradable or absorbable biocompatible materials for the gel/fluid carrier include, but are not limited to derivatives of polylactide, chondroitin sulfate (a proteoglycan component), polyesters, polyethylene glycols, polycarbonates, polyvinyl alcohols, polyacrylamides, polyamides, polyacrylates, polyesters, polyetheresters, polymethacrylates, polyurethanes, polycaprolactone, polyphophazenes, polyorthoesters, polyglycolide, copolymers of lysine and lactic acid, copolymers of lysine-RGD and lactic acid, dextran, dextrin, starch, cellulose, chitosan, demineralized bone matrix and the like and copolymers of the same. Among the biodegradable, biocompatible materials enumerated above, collagen is especially desirable.

The carrier can also be a non-biodegradable material formed by hydrating the triblock polymer poly(ethylene oxide)-poly(propylene oxide)-poly(ethylene oxide), which is commercially available under the Pluronic™ or Poloxamer™ tradenames. In addition, Sawhney et al., *Macromolecules*, 26:581–589 (1993), which is incorporated herein by reference, discloses synthesized macromers having a poly (ethylene glycol) central block, extended with oligomers of α-hydroxy acids such as oligo(d,l-lactic acid) or oligo (glycolic acid) and terminated with acrylate groups. The macromers can be rapidly polymerized with visible light in the presence of a non-toxic photoinitiator, to form crosslinked gels. The gels can degrade within a physiological environment upon hydrolysis of the oligo(α-hydroxy acid) regions into poly(ethylene glycol), α-hydroxy acid, and oligo(acrylic acid). The degradation rates can be tailored by appropriate choice of the oligo(α-hydroxy acid). The gel can be completely degraded within four months under physiological conditions. Another synthesized biodegradable block copolymeric material is disclosed in Japanese Patent No. 2-78629 (which is incorporated herein by reference), which is synthesized by transesterification of poly (lactic acid) (PLA) or poly(lactic acid)/glycolic acid (PLA/GA) and poly(ethylene glycol) (PEG).

The carrier for the constructs can be a gel matrix as described above. It can also be a liquid material or a gel material having a viscosity or density that is lower than the above-described ranges, but is capable of forming a suitable matrix in the physiological environment of an animal to be treated, e.g., in a human body. For this purpose, many polymers known in the art can be used. For example, U.S. Pat. Nos. 4,474,751 and 4,474,752, which are incorporated herein by reference, disclose proprietary polymers known as Tetronic® polyols. Such polymers can be dissolved in an aqueous base with a desired pH, and the solution can be injected subcutaneously or intramuscularly. Upon injection into a physiological environment, the aqueous solution can form a semi-solid gel at body temperature.

The Cells

In a preferred embodiment of this invention, the three-dimensional support construct may contain cells or tissue explants or cellular extracts therein, or have cells or tissue or cellular extracts attached thereto, which are intended for growth and further proliferation after being delivered into the body of the living subject. Cellular extracts that may be incorporated into the constructs, the carrier, or both include, but are not limited to, deoxyribonucleic acid (DNA), plasmids, ribonucleic acid (RNA), and growth factors. The cells and tissues to be incorporated in the construct can be homogeneous from one single source, or from different sources. When heterogeneous cells are used, the construct may be formed from two or more biocompatible materials, each supporting a different type of cell or tissue or the cells may be homogeneously distributed on constructs of the same biocompatible materials.

The selection of cells to be seeded in the three-dimensional construct depends on particular tissue engineering purposes. For example, if the composite of this invention is used for the reconstruction, repair or augmentation of a breast, breast tissue or cells such as vascular endothelial cells and smooth muscle cells can be used. Other cells, such as mesenchymal cells which include fibroblasts, chondrocytes, and adipocytes can also be used alone or in conjunction with endothelial or smooth muscle cells. Fat tissue can also be included in the constructs. For the repair of a spinal disc defect or injury, intervertebral disc cells can be desirable. In the case of repairing a bony defect, osteoblasts can be seeded in, e.g., polylactide beads and mixed with a carrier made of, e.g., alginate.

Various techniques for isolating cells or tissues from suitable sources are generally known in the art. The cells or tissues used in this invention are preferably autologous, i.e., obtained from the living subject being treated, or the cells may be allogeneic, i.e., obtained from a subject of same species as the subject being treated. The cells can also be xenogeneic, i.e., from a subject of different species.

In addition, the cells can also be treated in vivo or in vitro, before or after being incorporated into the cell construct. The cells may be cultured in vitro to expand in number or modified to change one or more characteristics. Methods for doing so should be apparent to those skilled in the art. For example, a porous construct with cells attached therein can be conveniently immersed in a suitable culture medium. To promote the growth and differentiation of the cells, suitable signal molecules can be added to the culture medium to promote cell adhesion, growth, and migration. Examples of such signal molecules include, but are not limited to, serum, growth factors, and extracellular matrix proteins.

The cells can also be genetically, physically or chemically modified in vitro. Genetic modification by molecular biology techniques is generally known in the art. Methods are also known in the art to modify the immunological characters of allogeneic or xenogeneic cells so that the cells are not substantially rejected by the host tissue when they are delivered to the area of interest. Immunologically inert cells, such as stem cells infant cells, and embryonic cells are preferably used to avoid immunological incompatibility.

Cells or tissues or cellular extracts can be incorporated into the carrier during the preparation of the fluid or gel. Cells or tissues or cellular extracts can be incorporated into the constructs during the formation of the constructs, for example, during the process of polymerization. Alternatively, the cells can be seeded into preformed porous constructs. Since the pores of the constructs can be fairly large as described above, cell seeding can be easily done, for example, by immersing the porous constructs for a period of time in a cell culture medium having cells to be seeded floating therein. The cell density in the medium and the period of time can be easily controlled to allow a desirable number of cells to attach within the porous construct. Typically, the medium contains from about $2\times10^6$ to about $5\times10^7$ cells per milliliter of construct preferably from about $4\times10^6$ to about $1\times10^7$ cells per milliliter of construct.

Construct Coatings

In some embodiments it is desirable to coat the porous construct with materials that promote cell adhesion and attachment to the structure of the porous construct. Examples of such materials include, but are not limited to, fibronectin, vitronectin, collagens, polylysine, laminins, polypeptides derived from these extra-cellular matrices, and other cell adhesion molecules. Such coatings can be done at any time, for example, coating on polymer precursors, coating of a prepared construct before seeding cells in vitro, or after seeding in vitro but before delivering the construct into the body of a living subject of interest. An example of coating is to coat porous beads such as porous polyglycolide beads and porous collagen beads with, e.g., a thin layer of an alginate-RGD hydrogel by cross-linking the hydrogel onto the beads.

Composite Signals

The construct and the carrier of this invention may also contain a signal for modifying cell adhesion, growth, or migration, preferably stimulating or promoting the adhesion, growth, or migration of the desirable cells, and/or inhibiting the adhesion, growth, or migration of the undesirable cells. The signals may be growth factors, hormones, extracellular matrix proteins and other cellular adhesion peptides identified in the extracellular matrix protein. Suitable growth factors may include, for example, epithelial growth factor (EGF), acidic or basic fibroblast growth factor (FGF), vascular endothelial growth factor (VEGF), hepatocyte growth factor (HGF), heparin binding growth factor (HGBF), transforming growth factor (TGF), nerve growth factor (NGF), muscle morphogenic factor (MMP), and platelet derived growth factor (PDGF). Examples of extracellular matrix proteins include fibronectin, collagens, laminins, and vitronectins, and the tri-peptide RGD (arginine-glycine-aspartate) that is found in many of the extracellular matrix proteins. A signal can also be included to induce the ingrowth of the desirable cells, e.g., smooth muscle cells and epithelial cells, in the surrounding body tissues. Preferably, compounds that inhibit undesired cells, such as cancerous cells and inflammatory cells are also included. The signals can be covalently linked to a biocompatible material in the construct or carrier, or associated with the construct or carrier by affinity, or linked to a material that itself can be covalently linked to or associated by affinity with a biocompatible material in the construct or carrier. Alternatively, the signals can be dispersed in or in admixture with the carrier and constructs.

The constructs and carrier should be sterilized before use. Examples of such techniques include, but are not limited to, UV irradiation, gamma irradiation, e-beam sterilization and sterilization using chemicals such as ethylene oxide. The sterilization method used must not substantially adversely affect the structures and properties of the constructs and carrier and their abilities to support cell growth and adhesion.

In accordance with one embodiment of the present invention, three-dimensional support constructs that do not contain cells or tissues therein are contemplated. Once delivered into a desired area of a living subject along with a gel matrix or a liquid or viscous fluid that forms a gel matrix or viscous fluid after the injection, the support constructs can provide support for adhesion, migration, and ingrowth of tissue cells in the surrounding area.

Delivery Method

The preferred method of delivery is by injection. As used herein, "injectable" means the composition of the present invention can be readily injected into a target area of the body of a living subject such as mammals, using any injection means including, but not limited to, needles, syringes, and the like. Preferably, the composition can be injected through a needle having a size of no greater than 18 gauge, or an equivalent device.

To form the injectable composition of the present invention, a plurality of constructs with or without cells or tissues or cellular extracts are mixed with and dispersed in a gel matrix with or without cells or a liquid, with or without cells, capable of forming a gel matrix after being injected into a patient. Typically, the volume ratio of constructs to gel matrix is from about 1:2 to about 5:1, preferably, from about 1:1 to about 4:1, more preferably from about 3:1 to about 4:1.

The injectable composite of the present invention can be injected into an area of a living subject to augment a tissue structure and to form new tissues therein. Thus, the injectable composition can be used for reconstruction, repair or augmentation purposes in cosmetic surgeries in, e.g., facial, nipple, and breast tissues. For example, the composition of this invention can be injected into an area where a cancerous breast tissue has been removed. For this purpose, porous constructs containing fat tissues, or normal vascular endothelial cells or smooth muscle cells isolated from the patient, or combinations thereof can be created and mixed with a suitable carrier to create an injectable composition, which can be injected into the defective area of the breast.

The present invention can also be used in correcting defects in, e.g., bones and spinal discs. In addition, the composition can also be useful in tissue reconstruction to form three-dimensional tissues in various organs such as pancreas, liver, kidney, etc. Further, the method of the present invention can also be used to treat certain diseases in mammals. For example, to treat insulin-deficient diabetes, pancreatic islets or cells which release a desirable level of insulin can be seeded into the constructs of this invention and injected into the patient's body along with a gel matrix. In this case, it is preferred to inject the composition into a relatively vascular site such as the subcutaneous space.

The present invention is further illustrated by the following non-limiting examples. This invention may, however, be embodied in many different forms and should not be construed as limited to the embodiments set forth herein; rather, this embodiment is provided so that this disclosure will be thorough and complete and will fully convey the scope of the invention to those skilled in the art.

EXAMPLE 1

Collagen beads with 400 to 700 micron diameter and 50 to 100 micron pores were dynamically loaded for 48 hours at an initial seeding level of $1 \times 10^6$ rat aortic smooth muscle cells (RASMC)/ml beads. They were then mixed and gelled in alginates of 0.5, 1.0, and 2.0% gel strengths following cultivation. Samples were labeled and monitored fluorescently for cellular activity at 2, 24, and 48 hours. Based on in vitro results, a 1.0 percent alginate gel was used with similarly cultivated beads for an in vivo study. Composites were similarly prepared. 1 ml of the composite was injected subcutaneously in each experimental female Lewis rat. As a control, a composite in which the beads do not have cells seeded was injected into a female Lewis rat. Samples were retrieved after 2, 4, and 6 weeks and assessed histologically using a series of cell-specific stains.

The in vitro studies demonstrated that the 2.0 percent gel did not allow the high cell viabilities and the low gel strength of 0.5 percent did not maintain the necessary polymeric form. The in vivo work demonstrated that the material can be readily injected and thus is clinically feasible. The alginate provided separation for the beads and maintained their even distribution. All composites showed minimal inflammation and minimal fibrous encapsulation, and they appeared to be able to readily conform to irregular defects. In addition, development of the seeded rat aortic smooth muscle cells within the beads was observed.

Although the foregoing invention has been described in some detail by way of illustration and example for purposes of clarity of understanding, it will be obvious that certain changes and modifications may be practiced within the scope of the appended claims.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

What is claimed is:

1. A composite for use into a living subject comprising:
   a biocompatible porous three-dimensional construct comprising a material selected from the group consisting of alginate, collagen, polylactide, polyethylene glycol, polycaprolactone, polycolide, polydioxanone, and derivatives and copolymers thereof and having a size no greater than about 1.5 mm in diameter distributed within a carrier,
   said carrier comprising a gel matrix or viscous fluid when injected into the body of a living subject said gel matrix or viscous fluid being selected from the group consisting of biodegradable materials and non-biodegradable materials, each having a viscosity of from 10 to 1000 cps, and
   cells disposed in said biocompatible three-dimensional construct,
   wherein the three-dimensional construct allows for the growth of the cells disposed therein and for the ingrowth and attachment of surrounding tissue cells of the living subject.

2. The composite of claim 1, wherein said three-dimensional construct further comprises a coating of a material selected from the group consisting of fibronectin, vitronectin, collagens, polylysine, laminins, alginate-RGD hydrogel and polypeptides derived from extra-cellular matrices.

3. The composite of claim 1, wherein said three-dimensional construct further comprises a signal for modifying cell adhesion, growth or migration.

4. The composite of claim 1, further comprising a signal selected from growth factors, hormones, extracellular proteins, and cell adhesion peptides.

5. A composite for use in a living subject comprising:
   a biocompatible three-dimensional construct comprising a material selected from the group consisting of alginate, collagen, polylactide, polyethylene glycol, polycaprolactone, polydioxanone, and derivatives, and copolymers thereof and having a diameter of about 1.5 mm or less distributed within a carrier,
   said carrier comprising a gel matrix or viscous fluid when injected into the body of a living subject, said gel matrix or viscous fluid being selected from the group consisting of biodegradable and non-biodegradable materials, each having a viscosity of from 10 to 1000 cps; and
   cells disposed in said carrier,
   such that when disposed within the living subject, the composite allows for growth of the cells disposed in said carrier and ingrowth of surround tissue cells.

6. The composite of claim 5, wherein said three-dimensional construct is a biodegradable or absorbable material.

7. The composite of claim 6, wherein said three-dimensional construct is a material selected from the group consisting of chitosan, agarose, alginate, collagen, hyaluronic acid, and carrageenan, demineralized bone matrix, and the like, and copolymers of the same.

8. The composite of claim 6, wherein said three-dimensional construct is a material selected from the group consisting of polylactide, chondroitin sulfate, polyesters, polyethylene glycols, polycarbonates, polyvinyl alcohols, polyacrylamides, polyamides, polyacrylates, polyetheresters, polymethacrylates, polyurethanes, polycaprolactone, polyphophazenes, polyorthoesters, polyglycolide, copolymers of lysine and lactic acid, and copolymers of lysine-RGD and lactic acid, and the like, and copolymers of the same.

9. The composite of claim 5, wherein said carrier is a biodegradable or absorbable material.

10. The composite of claim 9, wherein said carrier is a material selected from the group consisting of derivatives of polylactide, chondroitin sulfate, polyesters, polyethylene glycols, polycarbonates, polyvinyl alcohols, polyacrylamides, polyamides, polyacrylates, polyetheresters, polymethacrylates, polyurethanes, polycaprolactone, polyphophazenes, polyorthoesters, polyglycolide, copolymers of lysine and lactic acid, and copolymers of lysine-RGD and lactic acid, dextran, dextrin, starch, cellulose, demineralized bone matrix and the like and copolymers of the same.

11. The composite of claim 5, wherein said carrier is a material selected from the group consisting of chitosan, polylactide, chondroitin sulfate, polyesters, polyethylene glycol, and derivatives thereof.

12. The composite of claim 5, wherein said carrier is a non-biodegradable material.

13. The composite of claim 12, wherein said non-biodegradable carrier is a hydrated triblock polymer poly(ethylene oxide)-poly(propylene oxide)-poly(oxide).

14. The composite of claim 5, wherein the volume ratio of said three-dimensional construct to said carrier is from about 1:2 to about 5:1.

15. The composite of claim 5, wherein said three-dimensional construct further comprises a coating of a material selected from the group consisting of fibronectin, vitronectin, collagens, polylysine, laminins, alginate-RGD hydrogel and polypeptides derived from extra-cellular matrices.

16. The composite of claim 5, wherein said three-dimensional construct further comprises a signal for modifying cell adhesion, growth, or migration.

17. The composite of claim 5, further comprising a signal selected from growth factors, hormones, extracellular matrix proteins, and cell adhesion peptides.

18. The composite of claim 5, wherein said three-dimensional construct further includes cells dispersed therein.

19. A composite for use in a living subject comprising:
  a biocompatible porous three-dimensional construct comprising a material selected from the group consisting of alginate, collagen, polylactide, polyethylene glycol, polycaprolactone, polycolide, polydioxanone, and derivatives and copolymers thereof and having a size no greater than about 1.5 mm in diameter distributed within a carrier,
  said carrier comprising a liquid or viscous fluid capable of forming a gel matrix or viscous fluid when injected into the body of a living subject said gel matrix or viscous fluid being selected from the group consisting of biodegradable materials and non-biodegradable materials, each having a viscosity of from 10 to 1000 cps; and
  cells disposed in said biocompatible three-dimensional support construct and said carrier,
  wherein when disposed in the living subject, the composite allows for growth of the cells disposed therein and ingrowth of surround tissue cells.

20. The composite of claim 19, wherein said three-dimensional construct further comprises a coating of a material selected from the group consisting of fibronectin, vitronectin, collagens, polylysine, laminins, alginate-RGD hydrogel and polypeptides derived from extra-cellular matrices.

21. The composite of claim 19, wherein said three-dimensional construct further comprises a signal for modifying cell adhesion, growth, or migration.

22. The composite of claim 19, further comprising a signal selected from growth factors, hormones, extracellular matrix proteins, and cell adhesion peptides.

23. A method of providing cells or tissue in a living subject comprising injecting into an area of interest in said living subject in need of treatment thereof an effective amount of a composite having a diameter of about 1.5 mm or less comprising:
  (a) a biocompatible three-dimensional support construct comprising a material selected from alginate, collagen, polylactide, polyethylene glycol, polycaprolactone, polydioxanone, and derivatives and copolymers thereof and having a porous structure which supports cell adhesion, growth and migration, thereby providing for ingrowth of surrounding tissue cells of the living subject;
  (b) a carrier comprising a liquid or viscous fluid forming a gel matrix or viscous fluid when delivered into the body of a living subject; and
  (c) cells disposed in said composite.

24. The method of providing cells or tissue in a living subject according to claim 23 wherein said cells are disposed in said carrier, wherein said carrier embeds the cells dispersed therein and prevents undue compression of the construct.

25. The method of providing cells or tissue in a living subject according to claim 23 wherein said cells are disposed in said support construct.

26. The method of providing cells or tissue in a living subject according to claim 23 wherein said cells are disposed in said support construct and in said carrier, wherein said carrier embeds the cells dispersed therein and prevents undue compression of the construct.

27. The method of providing cells or tissue in a living subject according to claim 23, wherein said composite further comprises seeding said cell or tissue in said biodegradable or absorbable three-dimensional support construct; and culturing said cell or tissue in vitro.

28. The method of providing cells or tissue in a living subject according to claim 23, wherein said construct further comprises a signal for modifying cell adhesion, growth, or migration.

29. The method of providing cells or tissue in a living subject according to claim 23, further comprising a signal selected from growth factors, hormones, extracellular matrix proteins, and cell adhesion peptides.

30. The method of claim 23, wherein said carrier has a viscosity of from about 10 to about 1000 cps.

31. The method of claim 23, wherein said carrier is biodegradable.

32. The method of claim 23, wherein said carrier comprises a material selected from the group consisting of agarose, alginate, carreenan and chitosan, and derivatives thereof.

33. The method of claim 23, wherein the area of interest in said living subject is a spinal disc in the human.

34. The method of claim 23, wherein the area of interest in said living subject is a bone in the human.

35. The method of claim 23, wherein the area of interest in said living subject is a nipple in the human.

36. The method of claim 23, wherein the area of interest in said living subject is a breast in the human.

37. The method of claim 23, wherein the area of interest in said living subject is a face or head of the human.

38. The method of claim 23, wherein the area of interest in said living subject is cartilage.

39. The method of claim 23, wherein the area of interest in said living subject is trunk soft tissue.

40. The method of claim 23, wherein the area of interest in said living subject is temporomandibular region.

41. The method of claim 23, wherein the area of interest in said living subject is alveolar ridge region.

42. A method for repairing a defect in the breast of a female patient, comprising:
injecting into the breast area of a female patient in need of treatment thereof an effective amount of a composite comprising a biocompatible, biodegradable three-dimensional support construct having a diameter of about 1.5 mm or less distributed within a carrier and made of collagen and containing cells obtained from said patient and selected from the group consisting of fibroblasts, smooth muscle cells, endothelial cells, mesenchymal cells, and an alginate carrier, said carrier comprising a liquid or viscous fluid having a viscosity of from 10 to 1000 cps, such that upon injection the composite allows for the growth of the cells contained therein and for the ingrowth of surrounding tissue cells.

43. A method for repairing a defect in a breast of a female patient, comprising:
injecting in the breast area of a female patient in need of treatment thereof an effective amount of a composite comprising a biocompatible, biodegradable three-dimensional support construct having a diameter of about 1.5 mm or less distributed within a carrier and made of collagen and containing cells obtained from a cell bank and selected from the group consisting of fibroblasts, smooth muscle cells, endothelial cells, mesenchymal cells, and an alginate carrier, said carrier comprising a liquid or viscous fluid having a viscosity of from 10 to 1000 cps, such that upon injection the composite allows for the growth of the cells contained therein and for the ingrowth of surrounding tissue cells.

44. A method for repairing a defect in a breast of a female patient, comprising:
injecting in the breast area of a female patient in need of treatment thereof an effective amount of a composite comprising a biocompatible, biodegradable three-dimensional support construct having a diameter of about 1.5 mm or less distributed within a carrier and made of polylactide based material and containing cells obtained from said patient and selected from the group consisting of fibroblasts, smooth muscle cells, endothelial cells, mesenchymal cells, and an alginate carrier, said carrier comprising a liquid or viscous fluid having a viscosity of from 10 to 1000 cps, such that upon injection the composite allows for the growth of the cells contained therein and for the ingrowth of surrounding tissue cells.

45. A method for repairing a facial defect in a patient, comprising:
injecting into the face of a patient in need of treatment thereof an effective amount of a composite comprising a biocompatible, biodegradable three-dimensional support construct having a diameter of about 1.5 mm or less distributed within a carrier and made of collagen and containing cells obtained from said patient and selected from the group consisting of fibroblasts, smooth muscle cells, endothelial cells, mesenchymal cells, and an alginate carrier, such that upon injection the composite allows for the growth of the cells contained therein and for the ingrowth of surrounding tissue cells.

46. A method for repairing a facial defect in a patient, comprising:
injecting into the face of a patient in need of treatment thereof an effective amount of a composite comprising a biocompatible, biodegradable porous three-dimensional support construct having a diameter of about 1.5 mm or less and made from collagen and an alginate carrier, such that upon injection the porous support construct allows for ingrowth of surrounding tissue cells.

47. A method for repairing a defect in the nipple of a female patient, comprising:
injecting into the nipple area of the breast of a patient in need of treatment thereof an effective amount of a composite comprising a biocompatible, biodegradable porous three-dimensional construct having a diameter of about 1.5 mm or less and of collagen, and an alginate carrier, such that upon injection the porous support construct allows for ingrowth of surrounding tissue cells.

48. A method for repairing a spinal disc in a patient, comprising:
injecting into the spinal disc a composite comprising a biocompatible, biodegradable porous three-dimensional construct having a diameter of about 1.5 mm or less and of collagen, said construct containing intervertebral disc cells obtained from said patient, and an alginate carrier, such that upon injection the composite allows for the growth of the cells contained therein and for the ingrowth of surrounding tissue cells.

49. A method for repairing a defect in a bone of a patient, comprising:
injecting into the bone of a patient in need of treatment thereof an effective amount of a composite comprising a biocompatible, biodegradable three-dimensional construct having a diameter of about 1.5 mm or less and made from polylactide osteoblast cells obtained from said patient, and an alginate, such that upon injection the composite allows for the growth of the cells contained therein and for the ingrowth of surrounding tissue cells.

* * * * *